United States Patent [19]

Sachinvala et al.

[11] Patent Number: 5,449,773
[45] Date of Patent: Sep. 12, 1995

[54] PLATINUM COMPLEXES OF SUCROSE DERIVATIVES

[75] Inventors: Navzer D. Sachinvala; Hong Chen, both of Aiea; Eichii Furusawa, Honolulu, all of Hi.

[73] Assignee: Hawaiian Sugar Planters' Association, Aiea, Hi.

[21] Appl. No.: 377,220

[22] Filed: Jan. 24, 1995

Related U.S. Application Data

[62] Division of Ser. No. 906,462, Jun. 30, 1992, Pat. No. 5,410,036.

[51] Int. Cl.$^6$ .......................... C07H 3/04; C07H 3/10; C07H 5/04; C07F 15/00
[52] U.S. Cl. ...................... 536/121; 536/17.9; 536/55; 536/120; 556/137
[58] Field of Search .................. 536/17.9, 120, 121, 536/55; 556/137

[56] References Cited

U.S. PATENT DOCUMENTS

| | | | |
|---|---|---|---|
| 4,117,224 | 9/1978 | Khan et al. | 536/119 |
| 5,116,961 | 5/1992 | Sachinvala | 536/18.2 |
| 5,120,836 | 6/1992 | Sachinvala | 536/18.7 |
| 5,122,601 | 6/1992 | Sachinvala | 536/125 |
| 5,126,438 | 6/1992 | Sachinvala | 536/18.4 |
| 5,166,334 | 11/1992 | Sachinvala | 536/124 |

OTHER PUBLICATIONS

Chemical Abstracts, vol. 79, p. 349, Abstr. No. 146,755c, Khan et al. Carbohydrate Res. 30: 183–186, 1973.
March, Jerry Advanced Organic Chemistry, Second Edition McGraw-Hill Co., New York; 1977, p. 326.
Chiu et al. Carbohydrate Res. 100: 247–261, 1982.

*Primary Examiner*—Douglas W. Robinson
*Assistant Examiner*—Gary L. Kunz
*Attorney, Agent, or Firm*—Burns, Doane, Swecker & Mathis

[57] ABSTRACT

Bis(platinum) and tris(platinum) complexes derived from 6,6'-diamino-6,6'-dideoxy-1',2-anhydrosucrose and 1',6,6'-triamino-1',6,6'-trideoxy-2,3,3',4,4'-penta-O-methylsucrose are disclosed as possessing anti-tumor activity.

2 Claims, No Drawings

PLATINUM COMPLEXES OF SUCROSE DERIVATIVES

RELATED APPLICATIONS

This application is a divisional of application Ser. No. 07/906,462, filed Jun. 1992 now U.S. Pat. No. 5,410,036 issued Apr. 25, 1995.

FIELD OF THE INVENTION

The subject invention relates to novel sucrose ligands, methods for their preparation and the use thereof for complexation with metals or metal bearing compounds such as cisplatinum. The invention also relates to the use of these novel sucrose ligands as food bulking agents and to make acrylamide and methacrylamide crosslinking agents. The subject invention further relates to pharmaceutical compositions containing mono(-platinum), bis(platinum), and tris(platinum) complexes derived from these sucrose ligands and the use thereof in the treatment of cancers including testicular cancer, or as sensitizers for radiation therapy and during imaging of pathological tissues.

BACKGROUND OF THE INVENTION

The synthesis of sucrose derivatives and improved methods for synthesizing sucrose derivatives is an area of significant research given the abundance and inexpense of sucrose and its suitability as a starting material for making many different biologically and industrially useful compounds.

For example, amino sugars are well known components of antibiotics and antibacterial polysaccharides. Additionally, sucrose derivatives have recently been used to make monomers and polymers from sucrose. See, e.g., Fritschela et al., European Patent 0218150 (1987); Khan et al., Carbohydrate Research (1980), pp. 185–189; and commonly assigned U.S. Pat. No. 5,248,747 issued Sep. 28, 1993.

Thus, given the known biological and industrial applicability of sucrose derivatives, methods for providing novel sucrose derivatives and methods for their usage would be highly desirable.

Cis-diaminedichloroplatinum (II), cis-DDP, or cisplatin as it is commonly known in the art, is a platinum complex which was first prepared by Alfred Werner in 1893 (Z Anorg. Chem., 1893, 3,267). However, this compound was only of interest to inorganic chemists until Rosenberg and colleagues discovered in 1965 that this complex and several related complexes, specifically cis, cis-diamine-dichloro-trans-dihydroxoplatinum (IV) and cis-cis-trans-diaminetetrachloroplatinum (IV) have the ability to prevent DNA replication in E. coli and that such complexes may be used as antineoplastic agents. (It was found, however, that transplatin or trans-diaminedichloroplatinum (II), a related complex, does not comprise this activity.)

The structures of these complexes are set forth below.

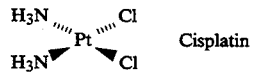

Cisplatin

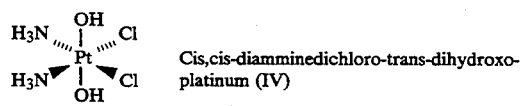

Cis,cis-diamminedichloro-trans-dihydroxoplatinum (IV)

-continued

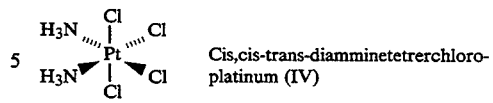

Cis,cis-trans-diamminetetrachloroplatinum (IV)

Transplatin (does not kill cancer cells)

Because of Rosenberg's discovery, cisplatin and its analogs have been the focus of extensive research. To date, well over 2,000 analogs of cisplatin have been published in the literature.

Cisplatin was approved for clinical usage in 1978 for the treatment of cancer and finds current use in the treatment of cancers, especially solid tumor types, such as testicular cancer, ovarian cancer, cervical cancer, head and neck cancer, and bladder cancer. However, by far its most significant usage in the treatment of testicular cancer since no other antineoplastic compound known behaves as specifically against a particular cancer as does cisplatin against testicular cancer.

Cisplatin, like other biologically active platinum (II) or platinum (IV) complexes, comprises the following generic structure:

As depicted in the above structure, the platinum atom is bound to two inert and two labile ligands which are mutually cis. The inert R-NH$_2$ ligands contain one or more hydrogen atoms which facilitate hydrogen binding to phosphate groups contained in the DNA helix and include, e.g., ammonia, alkylamines, alicyclic or aromatic amines, or chelating diamines. Suitable labile X groups include chloride, bisulfate, nitrate, water, acetate, oxalate, malonate and the like. Octahedral platinum (IV) complexes may contain only two chloride or hydroxyl ligands axially trans.

As noted, trans(platinum) complexes are not cytotoxic. In addition, bulky complexes containing amines and triamine ligands are not biologically active.

For illustrative purposes, various active, inactive, and second generation cisplatin analogs are depicted below:

Active complexes

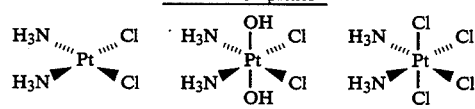

Inactive complexes

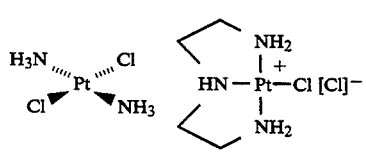

-continued

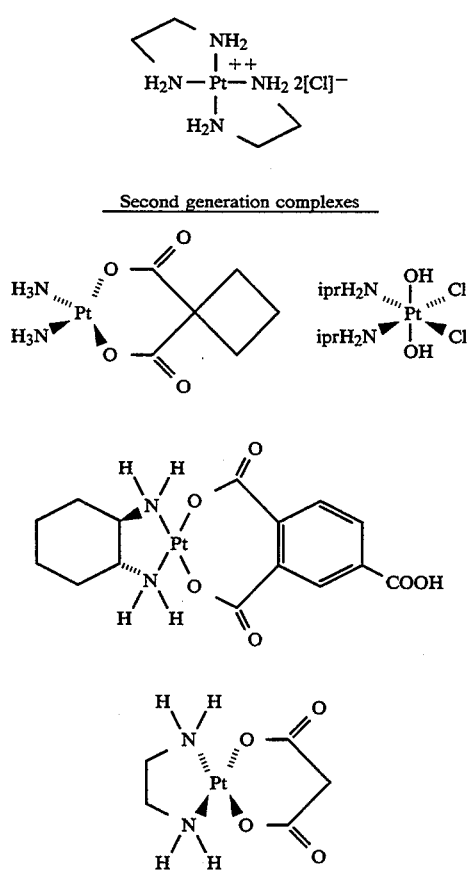

Second generation complexes

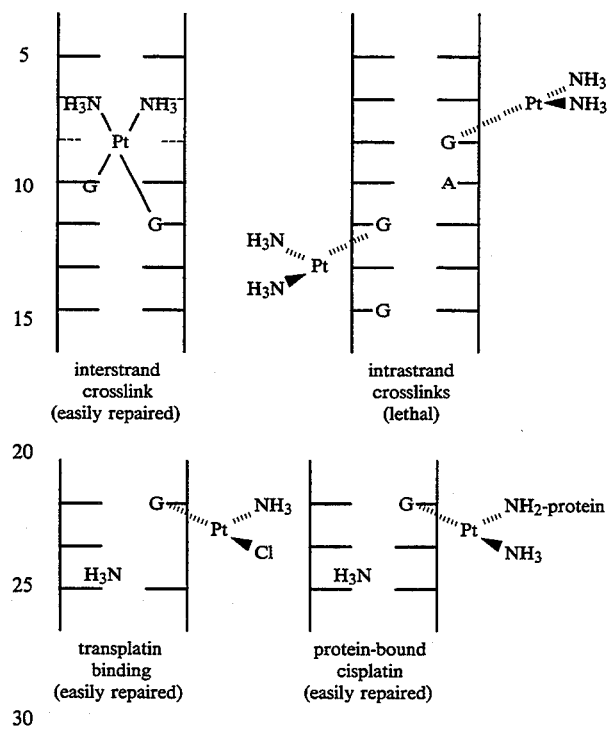

Binding modes of cis- and transplatin to DNA:

interstrand crosslink (easily repaired)

intrastrand crosslinks (lethal)

transplatin binding (easily repaired)

protein-bound cisplatin (easily repaired)

Cisplatin and related complexes exert their cytotoxicity by preventing DNA replication. However, it remains unclear as to how such complexes actually enter cells. It has long been assumed that cisplatin enters a cell by passive diffusion. However, this theory has fallen into disfavor recently since extensive evidence exists which indicates that accumulation of the drug may be modulated by means which are incompatible with simple passive diffusion. (See Andrews et al., *Cancer Cells*, Feb. 1990, Vol. 2, No. 2, pp. 35–43). However, classical proof for an active carrier system is lacking since accumulation is not saturable up to 3 mM cisplatin and cannot be inhibited with structural analogs. (Id. at 35).

Once cisplatin enters a cell, it hydrolyzes to form a diaquodiammino-platinum (II) complex, the substantial portion of which complexes with intracellular proteins. However, about one percent binds to the cellular DNA.

Cisplatin and other related platinum complexes bind to DNA by various means of which the intrastrand mode is both the most prevalent and the most stable. These modes of binding are depicted on the following page.

Of these it is the intrastrand mode which causes kinks to develop in the DNA strand which may prevent DNA replication (if the kinks remain unrepaired). Moreover, it is this prevention of DNA replication which is the mechanism by which cisplatin is eventually lethal to tumor cells.

As discussed supra, cisplatin is very effective in the treatment of some solid tumor type cancers. When used clinically, cisplatin is typically administered intravenously in a hypertonic saline solution or may be intraperitoneally injected directly into a solid tumor site.

However, despite its efficacy in the treatment of cancers, many significant problems remain with the clinical usage of this drug. For example, the cancer cells may develop a resistance to the cisplatin drug, e.g., by (i) developing mechanisms to preclude entry of the drug, (ii) detoxifying the intracellular complexes before they bind to the DNA, or (iii) removing of the platinum bound nucleotides from the DNA by DNA repair mechanisms.

Acquired cisplatin resistance may be reduced but not obviated by various methods including (i) administering increased amounts of the drug, (ii) administering cisplatin in combination with other antineoplastic agents, (iii) administering the drug directly into a tumor site, (iv) inducing hyperthermia, (v) depleting glutathione and other sulfur-rich intracellular proteins, (vi) developing analogs containing multiple cis(platinum) complexes, (vii) binding cisplatin to target specific ligands, or (viii) developing cisplatin complexes containing moieties having different mode or modes of cytotoxity than cisplatin. However, acquired cisplatin resistance is still a significant problem associated with clinical use of this drug.

Another problem with cisplatin is its relative low aqueous and serum solubility. This low solubility can result in low absorption, distribution in the tissues and the precipitation of platinum complexes in the kidneys causing nephrotoxicity and other toxicities including gastrointestinal, reproductive, hematologic, neurotoxicity and ototoxicity. The serum solubility of platinum complexes may be enhanced by oxidizing platinum (II) to platinum (IV) or by complexation to labile ligands such as acetates, oxalates, bisulfates and the like. However, insolubility is still a significant problem which inhibits the clinical efficacy of cisplatin.

Another problem associated with cisplatin is its limited utility. Administration of cisplatin only comprises substantial therapeutic benefit in a few specific human cancers, most particularly testicular cancer.

Yet another problem associated with cisplatin is that it inefficiently binds DNA. As discussed supra, only one percent of the intracellular platinum actually becomes bound to the DNA, and of this only the intrastrand bound platinum results in cytotoxicity.

Recently, various researchers have purported that cisplatin binding to DNA may be enhanced by constructing complexes containing multiple cisplatin moieties. Bis(platinum) complexes have been prepared wherein the cisplatins are bonded with a four to six straight carbon atom linker (Farrell, et al., *J. Am. Chem Soc.*, 1988, Vol. 110, 5018; Farrell et al., *Inorganic Chem.*, 1989, vol. 28, 3416; Roberts et al., *Nucleic Acids Research*, 1989, vol. 17, p. 9719; Qu et al., *J. Am. Chem. Soc.*, 1991, vol. 113, 4851).

Later research by Jones et al. (*J. Biol. Chem.*, 1991, vol. 266, p. 7101) indicates that endonuclease promoted excision of nucleotides from both DNA strands may in itself be cytotoxic, which lends credence to the belief that his(platinum) complexes will provide better anticancer agents.

However, unfortunately, while bis(platinum) complexes have been prepared of the type below using commercially available 1,4-diaminobutane, 1,5-diaminopentane, and 1,6-diaminohexane, and with chloride or malonate as the labils ligands, significant problems exist with the usage thereof.

$$\begin{array}{c} NH_3 \\ | \\ X-Pt-NH_2-(CH_2)_n-NH_2-Pt-X \\ | \\ X \end{array} \quad \begin{array}{c} NH_3 \\ | \\ \\ | \\ X \end{array}$$

where
n=4=1,4-diaminobutane
n=5=1,5-diaminopentane
n=6=1,6-diaminohexane and
x=chloride or malanate In particular, all of the complexes prepared using chloride were entirely insoluble which renders them unsuitable for clinical usage. Additionally, the malonate bis(platinum) complexes, while active, displayed delayed toxicity (Farrell et al., *J. Med. Chem.*, 1990, 33, 2174). Thus, it is clear that improved cisplatin complexes free from the above-discussed problems would be highly desirable.

OBJECTS AND SUMMARY OF THE INVENTION

It is an object of the invention to avoid or alleviate the problems of the prior art.

It is an object of the invention to obtain novel sucrose ligands.

It is an object of the invention to produce improved cisplatin complexes free from the problems of the prior art.

It is a specific object of the invention to obtain 1',6,6'-triazido-1',6,6'-trideoxy-2,3,3',4,4'-penta-O-methylsucrose, 1',6,6'-tri-O-methanesulfonyl-2,3,3',4,4'-penta-O-methylsucrose, 6,6'-diamino-6,6'-dideoxy-1',2-anhydrosucrose and 1',6,6'-triamino-1',6,6'-trideoxy-2,3,3',4,4'-penta-O-methylsucrose.

It is another object of the invention to provide novel methods for the preparation of sucrose ligands.

It is a specific object of the invention to provide novel methods for the preparation of 1',6,6'-triazido-1',6,6'-trideoxy-2,3,3',4,4'-penta-O-methylsucrose; 1',6,6'-tri-O-methanesulfonyl-2,3,3',4,4'-penta-O-methylsucrose; 6,6'-diamino-6,6'-dideoxy-1',2-anhydrosucrose and 1',6,6'-triamino-1',6,6'-trideoxy-2,3,3',4,4'-penta-O-methylsucrose.

It is an object of the invention to use sucrose containing compounds as novel ligands for complexation with metal or metal containing compounds, including cisplatin or its analogs.

It is a specific object of the invention to provide bis(platinum) and tris(platinum) complexes derived from 6,6'-diamino-6,6'-dideoxy-1',2-anhydrosucrose, 1',6,6'-triamino-1',6,6'-trideoxy-2,3,3',4,4'-penta-O-methylsucrose and 6,6'-diamino-6,6'-dideoxy-1',2,3,3',4,4'-hexa-O-methylsucrose.

It is a further object of the invention to provide pharmaceutical compositions containing said bis(platinum) or tris(platinum) complexes and use same for the treatment of cancer.

It is yet another object of the invention to provide novel mono(platinum) complexes derived from 6,6'-diamino-6,6'-dideoxy-1,2,3,3',4,4'-hexa-O-methylsucrose and to use said mono(platinum) complexes as radiation sensitizers in radiation therapy or for imaging pathological tissues by X-ray or NMR spectroscopy.

It is another object of the invention to use 1',6,6'-triamino-1',6,6'-trideoxy-2,3,3',4,4'-penta-O-methylsucrose as a substrate for making acrylamide and methacrylamide crosslinking agents and to use same to make acrylamide and methacrylamide gels.

It is still another object of the invention to provide improved compositions, e.g. food compositions containing 6,6'-diamino-6,6'-dideoxy-1',2-anhydrosucrose as a bulking agent.

Conventional cisplatin components are subject to problems including poor aqueous and serum solubility and insufficient DNA binding. In contrast, the present inventors have developed novel cisplatin complexes containing one or more cisplatin moieties and specific sucrose ligands including 6,6'-diamino-6,6'-dideoxy-1',2,3,3',4,4'-hexa-O-methylsucrose, 6,6'-diamino-6,6'-dideoxy-1',2-anhydrosucrose and 1',6,6'-triamino-1',6,6'-trideoxy-2,3,3',4,4'-penta-O-methylsucrose, which are highly soluble and which should bind DNA more efficiently because of the presence of multiple cis(platinum) moieties.

Therefore, the use of the sucrose cisplatin complexes of the present invention should result in improved methods for treating cancers such as testicular cancer.

DETAILED DESCRIPTION OF THE PREFERRED EMBODIMENTS OF THE INVENTION

As discussed supra, the present invention relates in part to novel sucrose derivatives, specifically 6,6'- diamino-6,6'-dideoxy-1',2-anhydrosucrose; 1',6,6'-tri-O-methanesulfonyl-2,3,3',4,4'-penta-O-methylsucrose; 1',6,6'-triazido-1',6,6'-trideoxy-2,3,3',4,4'-penta-O-methylsucrose; and 1',6,6'-triamino-1',6,6'-trideoxy-2,3,3',4,4'-penta-O-methylsucrose and methods for their syntheses.

Synthesis of 6,6'-Diamino-6,6'-dideoxy-1',2-anhydrosucrose 6,6'-Diamino-6,6'-dideoxy-1',2-anhydrosucrose comprises the following structure:

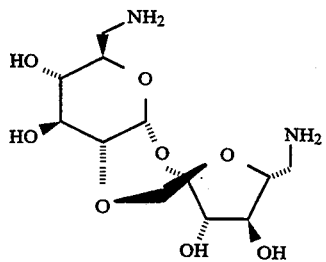

This compound may be synthesized by a process essentially comprising the following four steps:
i) Conversion of sucrose to 1',6,6'-tris-O-(triisopropylbenzene sulfonyl) sucrose, also called 1',6,6'-tri-O-tripsylsucrose;
ii) Conversion of 1',6,6'-tri-O-tripsylsucrose to 6,6'-diazido-6,6'-dideoxy-1',2-O-tripsylsucrose;
iii) Conversion of 6,6'-diazido-6,6'-dideoxy-1'-O-tripsylsucrose to 6,6'-diazido-6,6'-dideoxy-1',2anhydrosucrose; and
iv) Reduction of 6,6'-diazido-6,6'-dideoxy-1',2-anhydrosucrose to 6,6'-diamino-6,6'-dideoxy-1',2-anhydrosucrose.

Sucrose may be converted to 1',6,6'-tri-O-tripsylsucrose by methods which are known in the art. However, the preferred method will comprise the method of Almquist et al, as set forth in *J. Carbohydrates Nucleoside and Nucleotides*, 1974, vol. 1, 464, which reference is incorporated by reference in its entirety. This method advantageously results in yields of 1',6,6'-tri-O-tripsylsucrose which range from about 50 to 65 percent.

Similarly, the conversion of 1',6,6'-tri-O-tripsylsucrose to 6,6'-diazido-6,6'-dideoxy-1'-O-tripsylsucrose may be effected by methods available in the art. However, it is preferable that the procedure of Almquist et al (*Carbohydrate Research*, 1976, vol. 43, 33) be utilized since it results in yields of about 80 percent. This reference is also incorporated by reference in its entirety.

The third step will be effected by a modification of the process of Chiu et al described in *Carbohydrate Research*, 1982, vol. 100, p. 247.

Generally, this process will comprise reacting a solution containing the 6,6'-diazido-6,6'-dideoxy-1'-O-tripsylsucrose in an ethanolic sodium ethoxide solution which will be boiled under reflux for about 24 hours. In the operative example, a solution containing 0.50 g (0.76 mmol) was added to 10 ml 0.75M ethanolic sodium ethoxide and boiled under reflux for 24 hours. However, the relative amounts of these reactants and the heating times may be varied as desired.

After the solution is boiled under reflux it results in an amber solution which is preferably cooled to ambient temperatures and neutralized. Neutralization was effected using 6M aqueous hydrogen chloride by the present inventors, however, other known neutralizing agents may also be suitable. The resultant neutralized solution will then preferably be concentrated in vacuo and the product isolated therefrom.

Isolation may be effected using known and available methods for recovering sucrose derivatives. The present inventors flash-chromatographed the residue over a silica gel column and effected two elutions, the first using 6% methanol in methylene chloride, followed by a second elution with 10% methanol in methylene chloride. However, it is expected that the compound may be recovered using other available solvents such as, e.g., ethylacetate, 20% isopropanol in methylene chloride, or acetone/ethylacetate (1:1).

After the 6,6'-diazido-6,6'-dideoxy-1',2-anhydrosucrose is isolated it is preferably formulated as a solution in a suitable solvent. The present inventors used methanol in particular, however, other solvents may also be suitable including, e.g., ethanol, ethanol:water (1:1), isopropanol, or isopropanol:water (1:1).

This solution will then be reduced. This may, e.g., be accomplished using available reduction apparatus, e.g., the Parr Hydrogenation Apparatus using hydrogen and 10% palladium on carbon. This process results in the production of 6,6'-diamino-6,6'-dideoxy-1',2-anhydrosucrose in virtually 100% yields (quantitative yield).

This essentially four step process is a significant improvement over a previous seven step sequence starting with sucrose and resulting in 6,6'-diazido-6,6'-dideoxy-1',2 -anhydro-3,3',4,4'-tetra-O-benzoylsucrose which is exemplified in *Carbohydrate Research*, 1982, vol. 100, 247, and only results in 3.2 percent overall yield.

Synthesis of 1',6,6'-Tri-O-methanesulfonyl-2,3,3',4,4',penta-O-methylsucrose 1',6,6'-Tri-O-methanesulfonyl-2,3,3',4,4'-penta-O-methylsucrose may be synthesized by reacting a solution containing 2,3,3',4,4'-penta-O-methylsucrose and methanesulfonylchloride in dry pyridine under conditions suitable for the formation of 1',6,6'-trimethanesulfonyl-2,3,3',4,4'-penta-O-methylsucrose. The 2,3,3',4,4'-penta-O-methylsucrose is preferably prepared by the process described in commonly assigned U.S. Pat. No. 5,122,601 issued Jun. 16, 1992, and now allowed and which is hereby incorporated by reference in its entirety.

This reaction is preferably effected at about 0° C. Thereafter, the reaction mixture is preferably slowly allowed to attain ambient temperatures ($\cong 22°-25°$ C.) and then stirred for about 12 hours. The volatile contents are then removed in vacuo and the residue reconstituted using suitable solvents. Ethylacetate was used by the present inventors, however, other solvents may also be suitable.

The reconstituted residue is preferably then washed and dried. Saturated bicarbonate solution, saturated brine solution and water were utilized in the example, however, this washing process may be varied as desired using available washing procedures.

The washed residue will then preferably be dried, filtered, and concentrated in vacuo. Preferably after concentration the residue will be further purified by flash-chromatography using a silica gel column and eluted using suitable solvents. In particular, successive elutions were effected with 50% ethylacetate in hexane and 70% ethylacetate in hexane. However, other elutants may also be suitable, e.g., methylene chloride, or acetone in hexane.

Synthesis of 1',6,6'-Triazido-1',6,6'-trideoxy-2,3,3',4,4'-penta-O-methylsucrose This compound will essentially be prepared by reacting 1',6,6'-tri-O-methanesulfonyl-2,3,3',4,4'-penta-O-methylsucrose with an azide compound under conditions suitable for the formation of 1',6,6'-triazido-1',6 6'-trideoxy-2,3,3',4,4'-penta-O-methylsucrose. This reaction is preferably effected in dry hexamethylphosphoric triamide using sodium azide at about 120° C. with mixing for about 48 hours. Thereafter, the reaction mixture will preferably be cooled to ambient temperature, poured into ice water, and extracted with a solvent, preferably, ethylacetate.

The resultant organic layer should then preferably be washed, dried, and concentrated in vacuo to produce an oil. Washing may, e.g., be effected using a 4% aqueous sodium chloride solution and water.

The product is then be recovered, preferably, by flash-column chromatography on a silica gel column and eluted therefrom using suitable solvents, preferably, 50% ethylacetate in hexane.

Synthesis of 1',6,6'-triamino-1',6,6'-trideoxy-2,3,3',4,4'-penta-O-methylsucrose This product is produced by the reduction of 1',6,6'-triazido-1',6 6'-trideoxy-2,3,3',4,4'-penta-O-methylsucrose using a suitable reducing agent and under conditions suitable for the production of 1',6,6'-triamino-1',6,6'-trideoxy-2,3,3',4,4'-penta-O-methylsucrose.

Preferably, a solution of 1',6,6'-triazido-1',6 6'-trideoxy-2,3,3',4,4'-penta-O-methylsucrose in methanol will be reduced using hydrogen and 10% palladium on carbon effected in a hydrogenation apparatus.

However, alternatively, the 1',6,6'-triazido-1',6,6'-trideoxy-2,3,3',4,4'-penta-O-methylsucrose may be reduced by addition of lithium aluminum hydride in dry tetrahydrofuran. This reaction will preferably be effected at room temperature for about 2 hours. However, the reaction temperatures and time may be varied as desired.

Thereafter, the reaction mixture will preferably be treated with water followed by the addition of 15% aqueous sodium hydroxide solution. The resultant mixture is then allowed to settle and filtered. The filtrate is preferably then concentrated in vacuo and reconstituted to remove the lithium and aluminum salts. N,N'-Dimethylformamide is preferably used for reconstitution. However, other materials may also be used for reconstitution, e.g., N,N'-dimethylacetamide, or N-methylpyrrolidone. The resulting suspension may then be filtered and concentrated, e.g., by vacuum transfer resulting in the desired compound in quantitative yields.

The invention further relates to use of the described sucrose derivatives for complexation with heavy metals, and metal containing compounds, e.g., cobalt, iron, nickel, manganese, platinum, palladium, chromium, ruthenium, rhodium, iridium, technicium, and rhenium. Methods for complexation of ligands to metals or metal containing compounds are well known in the art and within the purview of the skilled artisan.

The invention in particular relates to bis(platinum) and tris(platinum) complexes derived from three sucrose ligands, namely: 6,6'-diamino-6,6'-dideoxy-1',2-anhydrosucrose (1); 1',6,6'-triamino-1',6 6'-trideoxy-2,3,3',4,4'-penta-O-methylsucrose (2); and 6,6'-diamino-6,6'-dideoxy-1',2,3,3',4,4'-hexa-O-methyl-sucrose (3). The invention further relates to mono(platinum) complexes derived from 6,6'-diamino-6,6'-dideoxy-1',2,3,3',4,4'-hexa-O-methylsucrose.

Essentially, bis(platinum) complexes derived from 6,6'-diamino-6,6'-dideoxy-1',2-anhydrosucrose will be synthesized having the generic structure on the following page.

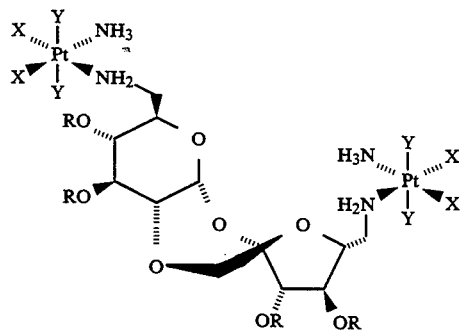

wherein if Pt is in oxidative state +2 (II) then;

X may, e.g., be chloride, malonate, oxalate, alkylidene malonate, cyclopropylmalonate, 2-bromoacetate, 2-iodoacetate, acrylate or methacrylate, and R may, e.g., be hydrogen, methyl, other alkyl groups or allyl groups, or wherein if Pt is in oxidation state +4 (IV) then;

X may be chloride,

Y may be hydroxyl, propionate, acrylate, butyrate, methacrylate or pentanoate and the like, and R may be hydrogen, methyl, other alkyl or allyl groups.

Tris(platinum) complexes derived from 1',6,6'-triamino-1',6,6'-trideoxy-2,3,3',4,4'-penta-O-methylsucrose will be synthesized having the following generic structure:

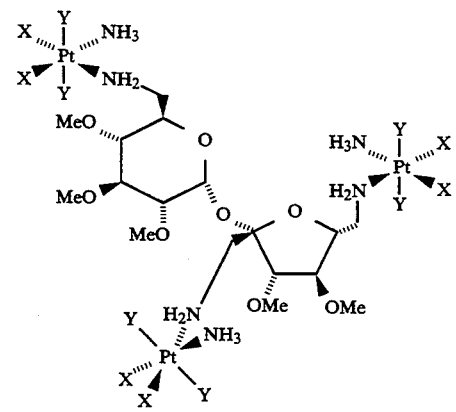

wherein if Pt is in oxidation state +2 (II) then

X may, e.g., be chloride, malonate, oxalate, alkylidene malonate, cyclopropylmalonate, 2-bromoacetate, 2-iodoacetate, acrylate or methacrylate, and R may, e.g., be methyl, other alkyl or allyl groups; or wherein if Pt is in oxidation state +4 (IV) then X may, e.g., be chloride, Y may, e.g., be hydroxyl, propionate, acrylate, methacrylate, butyrate, pentanoate and the like, and R may, e.g., be hydrogen, methyl, other alkyl or allyl groups.

Bis(platinum) complexes derived from 6,6'-diamino-6,6'-dideoxy-1',2,3,3',4,4'-hexa-O-methylsucrose will be synthesized having the following generic structure:

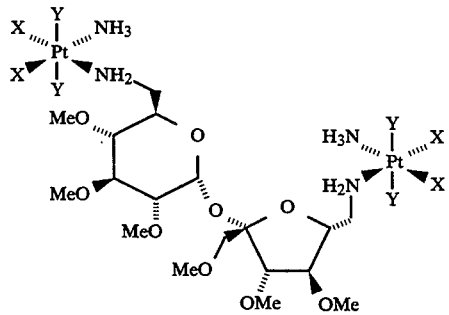

wherein if Pt is in oxidation state +2 (II) then

X may, e.g., be chloride, malonate, oxalate, alkylidene malonate, cyclopropylmalonate, 2-bromoacetate, 2-iodoacetate, acrylate or methacrylate, and R may, e.g., be $CH_3$, other alkyl or allyl groups, or wherein if Pt is in oxidation state +4 (IV) then X may, e.g., be chloride, Y may, e.g., be hydroxyl, or propionate, acrylate, methacrylate, butyrate, pentanoate and the like, and R may, e.g., be methyl, other alkyl or allyl groups.

Finally, mono(platinum) complexes may be made from 6,6'-diamino-6,6'-dideoxy-1',2,3,3',4,4'-hexa-O-methylsucrose having the following generic structure:

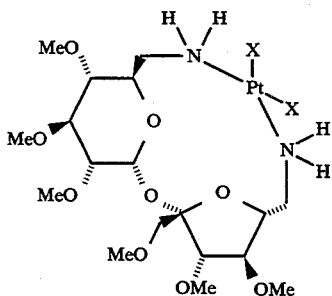

wherein X=iodide, oxalate, melonate or alkylidene melonate, cyclopropylmalonate.

The 6,6'-diamino-6,6'-dideoxy-1',2,3,3',4,4'-hexa-O-methylsucrose is prepared according to commonly assigned U.S. Pat. No. 5,120,836, issued Jun. 9, 1992, and which is hereby incorporated by reference in its entirety.

These complexes will be prepared by conventional methods for complexation of desired ligands to metal bearing compounds. Preferably, the mono(platinum) complexes of 6,6'-diamino-6,6'-dideoxy-1',2,3,3',4,4'-hexa-O-methylsucrose will be obtained using the methods of Dhara (*Indian J. Chemistry*, 1970, vol. 8, 193) and Reedjik et al (*Inorg. Chem.*, 1980, 19, 148), in order to obtain iodo, oxalate, malonate, and cyclopropylmalonate containing complexes. These references are incorporated by reference in their entirety.

The present inventors elected to synthesize the cyclopropylmalonyl complex, since the cyclopropylmalonyl moiety behaves like a Michael acceptor. Hence, it may itself alkylate DNA, bind to spindle fibers during mitosis, and arrest DNA replication and cell division. However, the other complexes should exhibit activity as well.

Applying the Kupchun model, which purports to explain how antitumor agents inhibit mitosis, deplete glutathione and sulfur-rich protein, and deplete enzymes responsible for DNA synthesis, and which theory essentially states that compounds which contain α,β-unsaturated carbonyls (Michael acceptors) are cytotoxic because they react with sulfhydryls in proteins; it was expected that the cyclopropylmalonyl containing complex would be more lethal than cisplatin. However, surprisingly, the cyclopropylmalonyl platinum complex of 6,6'-diamino-6,6'-dideoxy-1',2,3,3',4,4'-hexa-O-methylsucrose was not very toxic.

This is in contrast to cis-diaminecyclopropylmalonate platinum (II) below, which is two times more toxic than cisplatin:

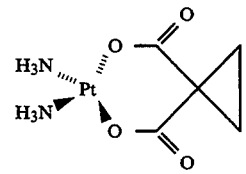

However, given this lack of toxicity, the subject mono(platinum) complexes should be well suited as radiation sensitizers or for imaging of pathological tissue. This will be accomplished by the labeling of these complexes with $^{13}C$ moieties, e.g., which are visualizable by nuclear magnetic resonance spectroscopy.

The subject mono(platinum) complexes should be superior to available radiation sensitizers given their lack of toxicity, and their high solubilities in both water and lipophilic solvents such as ethylacetate. Therefore, these compounds should be able to enter cells and remain their innocuously until they are expelled therefrom.

When using the subject mono(platinum) complexes as sensitizers for radiation therapy or during imaging of pathological tissues the sensitizers will preferably be administered to the subject by conventional modes of administration, e.g., intravenously intraperitoneally, orally, or other known methods. Preferably, the complexes will intravenously administered in an acceptable carrier, e.g., a saline solution. The complexes will be administered to the subject immediately prior to and during radiation therapy or imaging. The amount administered and the number of dosages will vary depending upon the length of radiation therapy, its intensity, etc.

The bis(platinum) complexes of the particular sucrose ligands may be made by conventional methods for complexing platinum compounds to ligands.

For example, bis(platinum) complexes of 6,6'-diamino-6,6'-dideoxy-1',2-anhydrosucrose may be made by modifying the procedure of Qu and Farrell (*Inorganic Chemistry*, 1989, 28, 3416). Essentially, this involves treatment of the anhydrodiaminosucrose with tetraethylammonium amminetrichloroplatinate (II) in methanol. This process provides the desired bis(platinum) complexes in about 50% yield.

The tris(platinum) complexes of the particular sucrose ligands may also be made by conventional methods for complexing platinum bearing compounds to desired ligands.

For example, tris(platinum) complexes of 1',6,6'-triamino-1',6,6'-trideoxy-2,3,3,4,4'-penta-O-methylsucrose compound with tetraethylammonium amminetrichloroplatinate (II) or potassium amminetrichloroplatinate. This provides the desired tris(platinum) complexes in about 45–50% yields.

The above-described bis(platinum) and tris(platinum) complexes will be suitable for the treatment of cancer, e.g., solid cancers such as testicular cancer, ovarian cancer, cervical cancer, head and neck cancer and bladder cancer.

These complexes may be administered by conventional methods for administering cisplatin derivatives. Preferably, the bis(platinum) and tris(platinum) complexes of the present invention will be used to make pharmaceutical compositions which contain an anticancer effective amount of the particular complex in combination with a pharmaceutically acceptable carrier such as a saline solution. These compositions will be administered by known methods, however, preferably the compositions will be administered intravenously, or intraperitoneally directly into the site of a tumor. Dosage effective amounts will vary dependent upon the activity of the particular complex, whether it contains two or three platinum atoms, the particular subject treated, etc. The determination of an effective dosage regimen is well within the level of skill in the art.

The complexes of the present invention may be administered singularly, or in combination. Further, the complexes of the present invention may be administered in combination with other anticancer agents.

As discussed supra, conventional cisplatin analogs only exert substantial cytotoxicity against specific tumors. It is expected that the cytotoxicity of the subject platinum complexes will be enhanced given that the subject complexes contain two or three cisplatin moieties.

However, it may further be desirable to conjugate the subject complexes to ligands which specifically bind targeted tumor cells and thereby produce platinum containing complexes which specifically bind target cells. Suitable ligands which are known and available in the art include monoclonal and polyclonal antibodies specific to tumor antigens, tumor cell receptors, cancer cell growth factors, etc.

This may be accomplished, e.g., by preparing platinum complexes containing cyclopropylmalonates which are well known to be homoenolate type Michael acceptors and to react with amine or sulfhydryl nucleophiles. Accordingly, cyclopropylmalonate containing complexes may be conjugated directly to tumor specific ligands or indirectly via bifunctional linkers which contain reactive amine or sulfhydryl groups. The resulting conjugates should exhibit cytotoxicity only toward the targeted tumor cells and exhibit negligible toxicity toward non-targeted cells, e.g., normal cells. These conjugates will be administered by the same methods as the bis and tris(platinum) complexes.

As discussed, 6,6'-diamino-6,6'-dideoxy-1',2-anhydrosucrose and 1',6,6'-triamino-1',6,6'-trideoxy-2,3,3'-4,4'-penta-O-methylsucrose are useful as ligands for preparing bis(platinum) and tris(platinum) complexes suitable for the treatment of cancer.

However, 6,6'-diamino-6,6'-dideoxy-1',2-anhydrosucrose has alternative utility as a bulking agent, e.g., in food compositions. This compound is tasteless, heat stable, non-metabolizable and being a sucrose derivative it exhibits a consistency like that of sucrose.

Therefore, it is well suited as a bulking agent, e.g., in artificially sweetened compositions, to provide the bulk consistency which sucrose would normally provide. Moreover, since this compound is water soluble and non-toxic, it may be used in bio-implants, e.g., breast implants as a substitute for more toxic compounds such as silicone.

1',6,6'-Triamino-1',6,6'-trideoxy-2,3,3',4,4'-penta-O-methylsucrose may also be used as a substrate to make triacrylamide and trimethacrylamide derivatives much like 1',6,6'-tri-methacryloyl-2,3,3',4,4'-penta-O-methylsucrose as disclosed in commonly assigned U.S. Ser. No. 07/877,813 filed on May 4, 1992, now U.S. Pat. No. 5,248,747 issued Sep. 28, 1993.

These trimethacrylamides and triacrylamides may be used to make acrylamide or methacrylamide gels which may be used for gel electrophoresis, ion-exchange, or for use in waste water purification. Such acrylamides and methacrylamides may also be used to make unwoven textiles or corrosion inhibitors.

In order to further illustrate the present invention and the advantages thereof, the specific examples are set forth below, it being understood that the same are intended to be illustrative and in nowise limitative.

EXAMPLES

General Methods

All reactions were conducted in dry glassware under an inert atmosphere. $^1H$ and $^{13}C$ NMR spectra were obtained using a General Electric GN Omega-500 instrument. Fast-atom bombardment (f.a.b.) mass spectra were recorded on VG instruments (Model 70 SE) using xenon as the bombarding gas. Optical rotations were obtained on a Jasco DIP-370 polarimeter at 598 nm. Elemental analyses were performed by Desert Analytics, Tucson, Ariz. Flash-column chromatography was performed according to Still et al. (Still, W. C.; Khan, M.; Mitra, A. *J. Org. Chem.*, 1978, 43, 2923) on silica gel (230 to 400 mesh). Radial chromatography was effected on some compounds by use of a Harrison Research Chromatotron (Model 7924T) using silica gel GF plate (0.40 cm thickness, 3.5 cm I.D., 11.0 cm O.D.). Compounds were detected on t.l.c. plates (silica gel 60, F 254, 0.25 mm, E. M. Science) by U. V. and/or by spraying with 10% phosphomolybdic acid in ethanol; $R_F$ values recorded here were determined on 10-cm strips of these plates. All organic reagents and solvents (reagent grade, Aldrich Chemical Co.) were purified and dried before use according to procedures outlined by Perrin et al (Perrin, D. D.; Armarego, W. F. L.; Perrin, D. R. *Purification of Laboratory Chemicals*, 2nd ed., Pergamon Press, Oxford, 1980). 6,6'-Diazido-6,6'-dideoxy-1'-O-tripsylsucrose (Reist, E. J. et al), 2,3,3',4,4'-penta-O-methylsucrose (Sachinvala, N. D. et al) and tetraethylammonium amminetrichloroplatinate (II) (Abrams, M. J. et al) were prepared by the following literature methods respectively, Almquist, R. D.; Reist, E. J. *Carbohydrate Research*, 1976, 46, 33; Sachinvala, N. D. "Synthesis of 2,3,3',4,4'-Penta-O-methylsucrose", U.S. Pat. No. 5,122,601 issued Jun. 16, 1992, Burns, Doane, Swecker & Mathis' Docket Number 011370-002; Sachinvala, N. D.; Niemczura, W. P.; Litt, M. H. *Carbohydrate Research*, 1991, 218, 237; Abrams, M. J.; Giandomenico, C. M.; Vollano, J. F.; Schwartz, D. A. *Inorganica Chimica Acta*, 1987, 131, 3. which are incorporated by reference in their entirety.

EXAMPLE 1

Synthesis of
6,6'-Diazido-6,6'-dideoxy-1',2-anhydrosucrose

The procedure of Chiu, A. K. B.; Gurjar, M. K.; Hough, L.; Sincharoenkul, L. V.; Richardson, A. C. *Carbohydrate Research*, 1982, 100, 247, was modified as shown below. A solution of 6,6'-diazido-6,6'-dideoxy-1'-O-tripsylsucrose (0.50 g, 0.76 mmol) in 10 ml 0.75M ethanolic sodium ethoxide was boiled under reflux for 24 hours. The resultant amber solution was cooled to 25° C., then neutralized with 6M aqueous hydrogen chloride and concentrated in vacuo. The residue was then flash-chromatographed over a column of silica gel (5×15 cm), eluted with 6% methanol in methylene chloride (2 liter), followed by elution with 10% methanol in methylene chloride (2 liter), at a flow rate of ca. 50 ml/min. Better chromatographic resolution of this product was achieved on a silica gel GF plate (0.40 cm thickness, 3.5 cm I.D., 11.0 cm O.D.) placed on the Chromatrotron (Model 7924T) with a solvent flow rate of 8 Ml/min. The isolated product weighed 0.21 g (0.57 mmol, 75 percent yield); m.p. 123.0° to 123.5° C.; $[\alpha]_d^{25}$ +113.6 (c 0.90, methanol); $R_F$ 0.17 in 10 percent methanol in methylene chloride; F.a.b. mass calc. for $C_{12}H_{18}N_6O_8$: 374.3; observed $[M+K]+=413$. 500 MHz $^1$H NMR and 125 MHz $^{13}$CNMR data are shown in Table 1.

Anal. Calc. for $C_{12}H_{18}N_6O_8H_2O$: C, 36.7; H, 5.1; N, 21.4. Found: C, 36.6; H, 5.2; N, 21.5.

On a large scale, it is difficult to separate 6,6'-diazido-6,6'-dideoxy-1',2-anhydrosucrose from the other reaction products on silica gel. It is therefore necessary to acetylate this compound, separate 6,6'-diazido-6,6'-dideoxy-3,3',4,4'-tetra-O-acetyl-1',2-anhydrosucrose on silica gel and again deacetylate the tetra-acetoxy product to obtain highly pure 6,6'-diazido-6,6'-dideoxy-1',2-anhydrosucrose. The detailed synthetic procedure is as follows: A solution of 6,6'-diazido-6,6'-dideoxy-1'-O-tripsylsucrose (14.6 g, 22 mmol) in 300 ml 0.75M ethanolic sodium ethoxide was boiled under reflux for 30 hours. The resultant amber solution was cooled to 25° C., then neutralized with 6M aqueous hydrogen chloride and concentrated in vacuo. The residue was dried in vacuo (0.01 mmHg) overnight, dissolved in dry pyridine (140 ml) and treated with acetic anhydride (18.7 ml, 198 mmol, ca. 3 equivalents/OH group, added dropwise at 0° C.). The reaction mixture was allowed to attain room temperature, stirred for 48 hours, and then the volatiles were removed by vacuum transfer. The residue was flash-chromatographed over a column of silica gel (7×15 cm) by eluting with 5% ethylacetate in methylene chloride, at a flow rate of ca. 150 ml/min. The isolated 6,6'-diazido-6,6'-dideoxy-3,3',4,4'-tetra-O-acetyl-1',2-anhydrosucrose (5.3 g, 9.7 mmol) was subsequently deacetylated with methanolic sodium methoxide (250 ml, 0.20M) at 25° C. for 16 hours. The resulting reaction mixture was neutralized with 6M aqueous hydrogen chloride and concentrated in vacuo. The residue was then flash-chromatographed over a silica gel column (7×15 cm), eluted with 10% methanol in methylene chloride at a flow rate of ca. 150 ml/min. to give 6,6'-diazido-6,6'-dideoxy-1',2-anhydrosucrose (3.2 g, 8.6 mmol) in 22% overall yield from sucrose.

EXAMPLE 2

Synthesis of
6,6'-Diamino-6,6'-dideoxy-1',2-anhydrosucrose

A solution containing 6,6'-diazido-6,6'-dideoxy-1',2-anhydrosucrose (0.374 g, 1.00 mmol) in methanol (50 ml) was reduced in a Parr Hydrogenation Apparatus (Model 3916 EG) using hydrogen (50 psig) and 10% palladium on carbon (30 mg), for 48 hours, to give 6,6'-diamino-6,6'-dideoxy-1',2-anhydrosucrose in quantitative yield. M.p. 158° to 161° C.; $[\alpha]_d^{25}$ ±89.2 (c 0.47, methanol); F.a.b. mass calc. for $C_{12}H_{22}N_2O_8$: 322.3; observed $[M+K]+=361.3$. 500 MHz $^1$H NMR and 125 MHz $^{13}$C NMR data are shown in Table 2.

Anal. Calc. for $C_{12}H_{22}N_2O_8$: C, 44.7; H, 6.9; N, 8.7. Found: C, 4.5; H, 7.0; N, 8.3.

EXAMPLE 3

Synthesis of
N,N,-bis[cis-amminedichloroplatinato]-6,6'-diamino-6,6'-dideoxy-1',2-anhydrosucrose The procedure of Qu, Y.; Farrell, N. *Inorganic Chemistry*, 1989, 28, 3417, was modified as shown below. To a solution of tetraethylammonium amminetrichloroplatinate (II) (1.57 g, 3.50 mmol) in methanol (50 ml) was added triethylamine (2 ml, dropwise, over 2 min) and a solution of 6,6'-diamino-6,6'-dideoxy-1',2-anhydrosucrose (0.564 g, 1.75 mmol) in methanol (5 ml was added over 5 min) and the mixture was allowed to stir for 24 hours. The resulting light yellow precipitate was filtered, washed with a small amount of methanol (ca. 5 ml) and recrystallized from N,N'-dimethylformamide to afford the title compound (0.82 g, 0.93 mmol) in 53 percent yield; F.a.b. mass calc. for $C_{12}H_{28}Cl_4N_4O_8Pt_2$: 888.6; observed $[M-Cl]+=853$. 500 MHz $^1$H NMR and 125 MHz $^{13}$C NMR data are shown in Table 3.

Anal. Calc. for $C_{12}H_{28}Cl_4N_4O_8Pt_2.3CH_3OH$: C, 18.3; H, 4.1; N, 5.7. Found: C, 18.6; H, 3.8; N, 5.8.

EXAMPLE 4

Synthesis of 1',6,6'-Tri-O-methanesulfonyl-2,3,3',4,4'-penta-O-methylsucrose

To a solution of 2,3,3',4,4'-penta-O-methylsucrose (6.18 g, 15.0 mmol) in dry pyridine (150 ml) was added methanesulfonylchloride (10.5 ml, 135 mmol) at 0° C. The mixture was allowed to come to ambient temperature slowly and was stirred for a period of 12 hours. The volatile contents were then removed in vacuo and the residue reconstituted in ethylacetate (500 ml). The ethylacetate layer was washed successively with saturated sodiumsbicarbonate solution (100 ml), saturated brine solution (2×100 ml) and water (100 ml), then dried over anhydrous sodium sulfate, filtered, and concentrated in vacuo. The residue was flash-chromatographed over a silica gel column (7×15 cm) and eluted with 50% ethylacetate in hexane (2 liter), followed by elution with 70% ethylacetate in hexane (2 liter), at a flow rate of 150 ml/min. The isolated product weighted 7.9 g (10.6 mmol, 71 percent yield); $R_F$ 0.21 in 75% ethylacetate in hexane; $[\alpha]_d^{25}$ ±42.9 (c 0.78, ethylacetate). 500 MHz $^1$H NMR and 125 MHz $^{13}$C NMR data are shown in Table 4.

Anal. Calc. for $C_{20}H_{38}O_{17}S_3$: C, 37.2; H, 5.9. Found: C, 37.0; H, 6.0.

EXAMPLE 5

Synthesis of 1',6,6'-Triazido-1',6,6',trideoxy-2,3,3',4,4'-penta-O-methylsucrose To a solution of 1',6,6'-tri-O-methanesulfonyl-2,3,3',4,4'-penta-O-methylsucrose (6.41 g, 9.92 mmol) in dry hexamethylphosphoric triamide (250 ml) was added sodium azide (19.4 g, 298 mmol) and the mixture stirred at 120° C. for 48 hours. The reaction mixture was then cooled to room temperature, poured into ice water (500 ml), and extracted with ethylacetate (3×200 ml). The combined organic layer was washed with 4% aqueous sodium chloride solution (2×200 ml), water (200 ml), dried over anhydrous magnesium sulfate, filtered, and concentrated in vacuo to provide an oil. Flash-column chromatography of the oil on a column of silica gel (7×15 cm) using 50% ethylacetate in hexane (3 liter) provided the desired product (3.72 g, 7.64 mmol) in 77 percent yield; $R_F$ 0.59 in 50% ethylacetate in hexane; F.a.b. mass calc. for $C_{17}H_{29}N_9O_8$: 487.4 ; observed $[M+K]^+ = 526.3$. 500 MHz $^1H$ NMR and 125 MHz $^{13}C$ NMR data are shown in Table 5.

Anal. Calc. for $C_{17}H_{29}N_9O_8$: C, 41.9; H, 6.0; N, 25.9. Found: C, 41.8; H, 6.0; N, 26.2.

EXAMPLE 6

Synthesis of 1',6,6'-Triamino-1',6 6'-trideoxy-2,3,3'-4,4'-penta-O-methylsucrose 1',6,6'-Triazido-1',6,6'-trideoxy-2,3,3',4,4'-penta-O-methylsucrose (0.501 g, 1.03 mmol) in methanol (60 ml) was reduced in a Parr Hydrogenation Apparatus (Model 3916 EG) using hydrogen (50 psig) and 10% palladium on carbon (30 mg) for 4.5 hours to give the title compound in 100 percent yield. Alternatively, 1',6,6'-triazido-1',6,6'-trideoxy-2,3,3',4,4'-penta-O-methylsucrose (0.501 g, 1.03 mmol) was reduced to the triamine upon addition of lithium aluminum hydride (0.376 g, 9.9 mmol) in dry tetrahydrofuran (30 ml) at 25° C. and stirred for 2 hours. The reaction mixture was then treated with water (10 ml, 1 ml/min.) followed by the addition of 15% aqueous sodium hydroxide solution (20 ml, 1 ml/min.). The resulting mixture was allowed to stand for 1 hour and filtered. The filtrate was concentrated in vacuo and the residue reconstituted in N,N'-dimethylformamide (15 ml) to precipitate all lithium and aluminum salts. The suspension was filtered and concentrated by vacuum transfer to afford the desired triamine in quantitative yield; $[\alpha]_d^{25}$ +118.7 (c 0.52, methanol). 500 MHz $^1H$ NMR and 125 MHz $^{13}C$ NMR data are shown in Table 6.

Anal. Calc. for $C_{17}H_{35}N_3O_8$: C, 49.9; H, 8.6; N, 10.3. Found: C, 49.5; H, 8.4; N, 10.7.

EXAMPLE 7

Synthesis of N,N',N''-tris[cis-amminedichloroplatinato]-1',6,6'-triamino-1',6,6'-trideoxy-2,3,3',4,4'-penta-O-methylsucrose The procedure of Qu, Y.; Farrell, N. *Inorganic Chemistry*, 1989, 28, 3417, was modified as follows. To a solution of tetraethylammonium amminetrichloroplatinate (II) (1.38 g, 3.09 mmol) in methanol (50 ml) was added triethylamine (2 ml, dropwise over 2 min.) and a solution of 1',6,6'-triamino-1',6,6'-trideoxy-2,3,3'-4,4'-penta-O-methylsucrose (0.421 g, 1.03 mmol) in methanol (5 ml, was added over 5 min.). The mixture was allowed to stir for 24 hours and the resulting light yellow precipitate filtered, washed with a small amount of methanol (ca. 5 ml) and recrystallized using dimethylformamide to afford the title compound (0.63 g, 0.50 mmol) in 49 percent yield. 125 MHz $^{13}C$ NMR data are shown in Table 7.

Anal. Calc. for $C_{12}H_{28}Cl_4N_4O_8Pt_2 \cdot 3CH_3OH$: C, 18.3; H, 4.1; N, 5.7. Found: C, 18.6; H, 3.8; N, 5.8.

EXAMPLE 8

Cytotoxicity Test of Diaminosucrose Platinum (II) Compounds on Human KB Cell Cultures The cytotoxicity of diaminosucrose platinum complexes was evaluated on human KB cell cultures as follows:

Graded doses of the respective diaminosucrose platinum (II) complexes tested contained in 0.1 ml of MEM medium were added to tube cultures of KB cells (contained in 1 ml of MEM medium with 4% fetal calf serum) immediately after seeding of ca. 2×10,000 cells/ml. The cells were then incubated for 5 to 14 days.

The incubated cultures were seeded every 3 days by 3 times dilution with the particular complex tested to maintain exponential cell growth. The results of these tests are shown in Table 8 which table sets forth the platinum complexes tested (by Sample No.), the concentration thereof, the incubation time, and the relative cytotoxic activity of the particular platinum complex tested.

The platinum complexes corresponding to the respective Sample Nos. are as follows:

Sample No. 1 (Cis-dichlorodiamine platinum),
Sample No. 2 (N-N'-(cis-dichloroplatinato)-6,6'-diamino-6,6'-dideoxy-1',2,3,3',4,4'-hexa-O-methylsucrose,
Sample No. 3 (N-N'-(cis-oxalatoplatinato)-6,6'-diamino-6,6'-dideoxy-1',2,3,3',4,4'-hexa-O-methylsucrose,
Sample No. 4 N,N'-(cis-malonatoplatinato)-6,6'-diamino-6,6'-dideoxy-1',2,3,3',4,4'-hexa-O-methylsucrose,
Sample No. 5 (N,N'-(cis-[1,1-cyclopropane dicarboxylato-platinato)]-6,6'-diamino-6,6'-dideoxy-1',2,3,3',4,4'-hexa-O-methylsucrose),
Sample No. 6 (N,N'-bis[cis-amminedichloroplatinato]-6,6'-diamino-6,6'-dideoxy-1',2-anhydrosucrose) and
Sample No. 7 (N,N',N''-tris[cis-amminedichloroplatinato]-1'6,6'-triamino-1',6,6'-trideoxy-2,3,3',4,4'-penta-O-methylsucrose.

After incubation the relative cytotoxic activity of the various platinum complexes was evaluated as follows:

Treated and untreated (control) tumor cell lines were viewed under the microscope and the number of dead cells quantified by visual means. Zero activity means that 100% of the treated cells survived, i.e., like the control. One + (1+) activity means that 25% of the treated cells appear to be dead, two + (2+) activity means that 50% of the treated cells appear to be dead, and three + (3+) activity means that 66% of the treated cells appear to be dead. Finally, four + (4+) means that between 66% to 100% of the treated cells appear to be dead.

The observed results indicate that Sample No. 1, 2, 6, and 7 are cytotoxic at minimum concentrations of 0.5 μg/ml (No. 1), 125 μg/ml (No. 2), 10 μg/ml (No. 6), and 10 μg/ml (No. 7), respectively when the cells are continuously cultured with said amount of the platinum complex. Thus, these results demonstrate the cytotoxic activity of the subject platinum complexes on human cancer cells.

EXAMPLE 9

Cytotoxic Test of Diaminosucrose Platinum (II) Compounds on Human KB Cell Cultures The experimental protocol of example 8 was repeated except using different platinum complexes designated Sample No. 8, Sample No. 9, Sample No. 10, and Sample No. 11. The respective platinum complexes corresponding to these Sample Nos. are as follows:

Sample No. 8 is cis-diammine-1,1-cyclopropanedicarboxylatoplatinum, Sample No. 9 is cis-(ethylenediamino- N,N')-1,1-cyclopropanedicarboxylatoplatinum, Sample No. 10 is cis-diammineitaconatoplatinum and Sample No. 11 is N-(amminedichloroplatinato)-2-aminoglucose.

The results of these tests are in Table 9. It can be seen that Sample No. 8 is significantly more cytotoxic to KB cells than is Cisplatin. Sample No. 9 appears to be more toxic than Sample No. 10 or Sample No. 6. The Sample No. 11 compound appears not to exhibit toxicity immediately but rather exhibits a delayed toxic response which occurs gradually during the incubation period.

EXAMPLE 10

Effect of Diaminosucrose Platinum (II) Compounds on Intraperitoneally Implanted Lewis Lung Carcinoma Cells in Mice Young adult syngeneic C57BL/6 mice (ca. 17–19 grams) were implanted intraperitoneally with $3-5\times10^5$ Lewis Lung tumor cells. The respective diaminosucrose platinum (II) compounds were then administered intraperitoneally in distilled water commencing the first day after tumor implantation.

The results of this study are set forth in Table 10. As with the previous examples, the respective platinum complexes tested have been designated by sample numbers. The sample number designates the same complexes as for the previous examples. These results show that sample No. 2 exhibits no antitumor activity or toxicity to the host at the dose tested (2 mg×2).

In contrast, Sample No. 6 at the same dose (2 mg×2) exhibited substantial antitumor activity but with significant reduction of body weight. Given this body weight loss, it would appear that this is the maximum tolerable dose. All of the mice treated, however, recovered the loss of body weight and were tumor-free by day 30.

Sample No. 7 at the dose (0.5 mg×4) also showed remarkable antitumor activity, but with moderate reduction of body weight. This is probably attributable to the smaller dosage. Larger dosages were not possible because of the solubility constraints. Thus, the above results indicate that the platinum complexes obtained by the present invention will be suitable for the treatment of cancer.

EXAMPLE 11

Cytoxicity Test of Sucrose Mono(platinum), Bis(platinum) & Tris(platinum) Complexes on Human KB Cell Cultures Graded doses of platinum complexes contained in 0.1 ml of MEM medium were added to tube cultures of KB cells (in ml of MEM medium with 4% fetal calf serum) immediately after seeding of ca. $2\times10,000$ cells/ml, and then incubated for 5 to 14 days. Cultures were seeded after 3 days by 3 times dilution with the platinum complex in order to maintain exponential growth.

The platinum complexes tested were cis-platin, a mono(platinum) complex of 6,6'-diamino-6,6'-dideoxy-1',2,3,3',4,4'-hexa-O-methylsucrose, a bis(platinum) complex of 6,6'-diamino-6,6'-dideoxy-1',2-anhydrosucrose and a tris(platinum) complex of 1',6,6' -triamino-1',6,6'-trideoxy-2,3,3',4,4'-penta-O-methylsucrose.

The results of this study are shown in Table 11. It can be seen that cisplatin, the sucrose bis(platinum) complex and the sucrose tris(platinum) complex were cytotoxic at the minimum concentrations of 0.5 μg/ml, 10 μg/ml and 10 μg/ml, respectively. Thus, these sucrose complexes exhibit comparable activity to cisplatin and should be suitable for the treatment of cancer.

EXAMPLE 12

Effect of Sucrose Mono(platinum), Bis(platinum), & Tris(platinum) Complexes on Intraperitoneally Implated Lewis Lung Carcinoma in Mice Lewis Lung tumor cells ($3-5\times10^5$) were inoculated intraperitoneally (i.p.) into young adult syngeneic C57BL/6 mice (ca. 17–19g body weight). Administration of the platinum complexes (contained in 0.1 ml of distilled water) was started on day 1 after tumor implantation. The respective sucrose mono(platinum), sucrose bis(platinum) and sucrose tris(platinum) complexes are the same as in the previous example.

The results of this study are depicted in Table 12. These results show that the sucrose mono(platinum) complex at a dose of (2 mg×2) exhibited no antitumor activity nor toxicity to the host. In contrast, the sucrose bis(platinum) complex at dose (2 mg×2) exhibited remarkable antitumor activity but with significant reduction of body weight. This appeared to be the maximum tolerable dosage. All the mice treated gradually recovered from the toxicity; however, 2 mice died of tumor growth on days 32 and 35. Three mice survived healthy and tumor-free up to the end of the observation period (day 50).

Similarly, the sucrose tris(platinum) complex at dose (0.5 mg×4) exhibited remarkable antitumor activity but with moderate .reduction in body weight. This is probably not the maximum nontoxic dosage, owing to the limited solubility of the sucrose tris(platinum) complex in water. Two mice died of tumor growth on day 22 and day 27. Three mice survived tumor-free until the end of the observation period (day 50).

The survival days of the individual mice tested were as follows:
Experiment 1
Control: 11, 13, 13, 15, 18
Mono(platinum): 13, 13, 14, 14, 15
Bis(platinum): 32, 35, >50, >50, >50
Experiment 2
Control: 10, 10, 11, 11, 12, 13
Tris(platinum): 22, 27, >50, >50, >50

EXAMPLE 13

Effect of Dose of Sucrose Bis(platinum) Complex on Intraperitoneally Implanted Lewis Lung Carcinoma in Mice The effect of dosage of the sucrose bis(platinum) complex on intraperitoneally implanted Lewis lung carcinoma cells was evaluated in mice. Lewis lung carcinoma cells ($10^5$) were inoculated intraperitoneally (i.p.) into syngeneic mice (ca. 17 g body weight). Administration of the complex (in 0.1 ml of distilled water) was effected on day 2 and day 4 after implantation.

The results are shown in Table 13. The sucrose bis(platinum) complex at a dose of 0.1 mg×2 (1/20 the dosage in the previous example) exhibited significant antitumor activity. Three mice survived healthy and tumor-free up to the end of the observation period (day 50).

EXAMPLE 14

Effect of Dose of Sucrose Bis(platinum) Complex on P388 Leukemia in Syngeneic DBA/2 Mice The effect of dose of sucrose bis(platinum) complex on P388 leukemia cells in syngeneic DBA/2 mice was evaluated. A 0.1 ml of 10× dilution of P388 ascites (ca. $10^6$ cells) was injected intraperitoneally (i.p.) into syngeneic DBA/2 mice (ca. 20 g body weight). The i.p. administration was effected on day 1 only. The bis(platinum) complex (1.0 mg/0.1 ml distilled water) had been stored for 77 days at 4° C. before administration.

The results of this study are shown in Table 14. These results indicate that the sucrose bis(platinum) complex at a dose of 2 mg showed significant antitumor activity; however, a dose of 0.1 mg exhibited no antitumor activity.

The sucrose bis(platinum) complex at high doses (still not toxic systemically) exhibited definite antitumor activity against P388 leukemia in mice. This activity is comparable to that of cisplatin against P388 leukemia. This evidence would indicate that the sucrose bis(platinum) complex should be suitable as a therapeutic agent for the treatment of cancer in humans.

EXAMPLE 15

Effect of Sucrose Bis(platinum) Complex on P388 Leukemia in Syngeneic DBA/2 Mice The effect of the sucrose bis(platinum) complex on P388 leukemia cells in syngeneic DBA/2 mice was further evaluated. A 0.1 ml of 10× dilution of P388 ascites (ca. $3 \times 10^5$ cells) was injected intraperitoneally (i.p.) into syngeneic DBA/2 mice (ca. 20 g body weight. The i.p. administration was effected on day 1 only. The bis(platinum) complex had been stored for two months in distilled water at 4° C. before administration. The results of this study are in Table 15. These results indicate that the sucrose bis(platinum) complex at a dose of 1.0 exhibited significant antitumor activity with prolongation of survival time 84% over the controls, and with one mouse appearing cured. Thus, these results provide further evidence that the subject bis(platinum) complexes should be suitable for the treatment of cancer.

TABLE 1

500 MHz $^1$H NMR and 125 MHz $^{13}$C NMR Data (in N,N'-dimethylformamide-d$_7$) for 6,6'-diazido-6,6'-dideoxy-1',2-anhydrosucrose

| $^{13}$C | | $^1$H | | |
|---|---|---|---|---|
| $C_1$ | 91.356 | $H_1$ | 5.4008 | $3_{J1,2} = 3.41$ |
| $C_2$ | 74.765 | $H_2$ | 3.4865 | $3_{J2,3} = 9.51$ |
| $C_3$ | 66.854 | $H_3$ | 4.1561 | $3_{J3,4} = 9.49\ 3_{J3,3OH} = 5.04$ |
| $C_4$ | 71.601 | $H_4$ | 3.3139 | $3_{J4,5} = 9.74\ 3_{J4,4OH} = 4.91$ |
| $C_5$ | 73.872 | $H_5$ | 3.9806 | $3_{J5,6a} = 2.01\ 3_{J5,6b} = 6.05$ |
| $C_6$ | 52.137 | $H_{6a}$ | 3.5158 | $2_{J6a,6b} = -13.16$ |
| | | $H_{6b}$ | 3.4944 | |
| $C_{1'}$ | 61.776 | $H_{1'a}$ | 3.9490 | $2_{J1'a,1'b} = -12.36$ |
| | | $H_{1'b}$ | 3.4526 | |
| $C_{2'}$ | 104.102 | | | |
| $C_{3'}$ | 79.085 | $H_{3'}$ | 3.6706 | $3_{J3',4'} = 8.14\ 3_{J3',3'OH} = 8.34$ |

TABLE 1-continued

500 MHz $^1$H NMR and 125 MHz $^{13}$C NMR Data (in N,N'-dimethylformamide-d$_7$) for 6,6'-diazido-6,6'-dideoxy-1',2-anhydrosucrose

| $^{13}$C | | $^1$H | | |
|---|---|---|---|---|
| $C_{4'}$ | 76.134 | $H_{4'}$ | 4.0948 | $3_{J4',5'} = 7.13\ 3_{J4',4'OH} = 5.44$ |
| $C_{5'}$ | 81.474 | $H_{5'}$ | 3.8748 | $3_{J5',6'a} = 3.38\ 3_{J5',6'b} = 7.06$ |
| $C_{6'}$ | 54.544 | $H_{6'a}$ | 3.5545 | $3_{J6'a,6'b} = -13.18$ |
| | | $H_{6'b}$ | 3.4127 | |
| | | $OH_3$ | 5.2950 | |
| | | $OH_4$ | 5.4959 | |
| | | $OH_{3'}$ | 5.4573 | |
| | | $OH_{4'}$ | 5.6955 | |

TABLE 2

500 MHz $^1$H NMR and 125 MHz $^{13}$C NMR Data (in N,N'-dimethylformamide-d$_7$) for 6,6'-diamino-6,6'-dideoxy-1',2-anhydrosucrose

| $^{13}$C | | $^1$H | | |
|---|---|---|---|---|
| $C_1$ | 91.317 | $H_1$ | 5.349 | $3_{J1,2} = 3.66$ |
| $C_2$ | 75.057 | $H_2$ | 3.416 | $3_{J2,3} = 9.76$ |
| $C_3$ | 67.087 | $H_3$ | 4.144 | $3_{J3,4} = 9.14$ |
| $C_4$ | 72.649 | $H_4$ | 3.308 | $3_{J4,5} = 9.16$ |
| $C_5$ | 74.833 | $H_5$ | 3.681 | $3_{J5,6a} = 4.27\ 3_{J5,6b} = 7.94$ |
| $C_6$ | 43.914 | $H_{6a}$ | 2.889 | $2_{J6a,6b} = -13.74$ |
| | | $H_{6b}$ | 2.802 | |
| $C_{1'}$ | 62.087 | $H_{1'a}$ | 3.936 | $2_{J1'a,1'b} = -12.21$ |
| | | $H_{1'b}$ | 3.371 | |
| $C_{2'}$ | 103.588 | | | |
| $C_{3'}$ | 79.707 | $H_{3'}$ | 3.615 | $3_{J3',4'} = 7.94$ |
| $C_{4'}$ | 77.047 | $H_{4'}$ | 4.048 | $3_{J4',5'} = 7.71$ |
| $C_{5'}$ | 84.483 | $H_{5'}$ | 3.675 | $3_{J5',6'a} = 3.45\ 3_{J5',6'b} = 7.66$ |
| $C_{6'}$ | 46.526 | $H_{6'a}$ | 2.823 | $3_{J6'a,6'b} = -13.35$ |
| | | $H_{6'b}$ | 2.799 | |

TABLE 3

500 MHz $^1$H NMR and 125 MHz $^{13}$C NMR Data (in N,N'-dimethylformamide-d$_7$) for N,N'-bis[cis-amminedichloroplatinato]-6,6'-diamino-6,6'-dideoxy-1',2-anhydrosucrose

| $^{13}$C | | $^1$H | | |
|---|---|---|---|---|
| $C_1$ | 91.269 | $H_1$ | 5.485 | $3_{J1,2} = 3.79$ |
| $C_2$ | 74.989 | $H_2$ | 3.480 | $3_{J2,3} = 9.24$ |
| $C_3$ | 67.349 | $H_3$ | 4.144 | $3_{J3,4} = 9.72$ |
| $C_4$ | 72.368 | $H_4$ | 3.240 | $3_{J4,5} = 9.51$ |
| $C_5$ | 73.018 | $H_5$ | 4.426 | $3_{J5,6a} = 3.81\ 3_{J5,6b} = 7.11$ |
| $C_6$ | 48.487 | $H_{6a}$ | 3.293 | $3_{J6a,6b} = -13.12$ |
| | | $H_{6b}$ | 2.601 | |
| $C_{1'}$ | 62.048 | $H_{1'a}$ | 4.000 | $3_{J1'a,1'b} = -12.21$ |
| | | $H_{1'b}$ | 3.461 | |
| $C_{2'}$ | 104.044 | | | |
| $C_{3'}$ | 78.998 | $H_{3'}$ | 3.762 | $3_{J3',4'} = 6.97$ |
| $C_{4'}$ | 81.367 | $H_{4'}$ | 4.161 | $3_{J4',5'} = 6.71$ |
| $C_{5'}$ | 77.047 | $H_{5'}$ | 4.169 | $3_{J5',6'a} = 3.61\ 3_{J5',6'b} = 6.93$ |
| $C_{6'}$ | 51.103 | $H_{6'a}$ | 3.106 | $3_{J6'a,6'b} = -12.89$ |
| | | $H_{6'b}$ | 2.921 | |

TABLE 4

500 MHz $^1$H NMR and 125 MHz $^{13}$C NMR Data (in Acetone-d$_6$) for 1',6,6'-Tri-O-methanesulfonyl-2,3,3',4,4'-penta-O-methylsucrose

| $^{13}$C | | $^1$H | | |
|---|---|---|---|---|
| $C_1$ | 90.434 | $H_1$ | 5.6138 | $3_{J1,2} = 3.59$ |
| $C_2$ | 82.117 | $H_2$ | 3.1778 | $3_{J2,3} = 8.86$ |
| $C_3$ | 84.232 | $H_3$ | 3.4026 | $3_{J3,4} = 9.19$ |
| $C_4$ | 76.669 | $H_4$ | 3.0840 | $3_{J4,5} = 10.07$ |
| $C_5$ | 70.575 | $H_5$ | 4.0508 | $3_{J5,6a} = 2.07$ |
| | | | | $3_{J5,6b} = 5.17$ |
| $C_6$ | 70.036 | $H_{6a}$ | 4.4891 | $2_{J6a,6b} = -10.98$ |
| | | $H_{6b}$ | 4.3541 | |
| $C_{1'}$ | 69.777 | $H_{1'a}$ | 4.2891 | $2_{J1'a,1'b} = -11.29$ |
| | | $H_{1'b}$ | 4.2265 | |
| $C_{2'}$ | 103.389 | | | |
| $C_{3'}$ | 85.903 | $H_{3'}$ | 4.0072 | $3_{J3',4'} = 7.64$ |

TABLE 4-continued

500 MHz $^1$H NMR and 125 MHz $^{13}$C NMR Data (in Acetone-d$_6$) for 1',6,6'-Tri-O-methanesulfonyl-2,3,3',4,4'-penta-O-methylsucrose

| $^{13}$C | | $^1$H | | |
|---|---|---|---|---|
| $C_{4'}$ | 83.648 | $H_{4'}$ | 3.9195 | $^3J_{4',5'} = 7.63$ |
| $C_{5'}$ | 79.496 | $H_{5'}$ | 4.1001 | $^3J_{5',6'a} = 7.71$ |
| | | | | $^3J_{5',6'b} = 2.92$ |
| $C_{6'}$ | 71.470 | $H_{6'a}$ | 4.5545 | $^3J_{6'a,6'b} = -11.37$ |
| | | $H_{6'b}$ | 4.4212 | |
| OMe$_2$ | 59.119 | OMe$_2$ | 3.483 | |
| OMe$_3$ | 60.716 | OMe$_3$ | 3.550 | |
| OMe$_4$ | 60.597 | OMe$_4$ | 3.530 | |
| OMe$_{3'}$ | 59.044 | OMe$_{3'}$ | 3.535 | |
| OMe$_{4'}$ | 58.828 | OMe$_{4'}$ | 3.471 | |
| MsMe$_{1'}$ | 37.599 | MsMe$_{1'}$ | 3.200 | |
| MsMe$_6$ | 37.308 | MsMe$_6$ | 3.150 | |
| MsMe$_{6'}$ | 37.340 | MsMe$_{6'}$ | 3.142 | |

TABLE 5

500 MHz $^1$H NMR and 125 MHz $^{13}$C NMR Data (in Acetone-d$_6$) for 1',6,6'-Triazido-1',6,6'-trideoxy-2,3,3',4,4'-penta-O-methylsucrose

| $^{13}$C | | $^1$H | | |
|---|---|---|---|---|
| $C_1$ | 90.466 | $H_1$ | 5.6092 | $^3J_{1,2} = 3.58$ |
| $C_2$ | 82.137 | $H_2$ | 3.1686 | $^3J_{2,3} = 9.72$ |
| $C_3$ | 83.805 | $H_3$ | 3.3964 | $^3J_{3,4} = 8.88$ |
| $C_4$ | 80.773 | $H_4$ | 3.0605 | $^3J_{4,5} = 10.05$ |
| $C_5$ | 71.276 | $H_5$ | 3.9420 | $^3J_{5,6a} = 2.49$ |
| | | | | $^3J_{5,6b} = 5.52$ |
| $C_6$ | 52.586 | $H_{6a}$ | 3.7000 | $^2J_{6a,6b} = -13.15$ |
| | | $H_{6b}$ | 3.4527 | |
| $C_{1'}$ | 55.316 | $H_{1'a}$ | 3.6651 | $^2J_{1'a,1'b} = -13.36$ |
| | | $H_{1'b}$ | 3.4182 | |
| $C_{2'}$ | 105.278 | | | |
| $C_{3'}$ | 86.703 | $H_{3'}$ | 3.9798 | $^3J_{3',4'} = 7.36$ |
| $C_{4'}$ | 85.141 | $H_{4'}$ | 3.8868 | $^3J_{4',5'} = 7.31$ |
| $C_{5'}$ | 80.258 | $H_{5'}$ | 4.0045 | $^3J_{5',6'a} = 8.50$ |
| | | | | $^3J_{5',6'b} = 3.43$ |
| $C_{6'}$ | 54.081 | $H_{6'a}$ | 3.8261 | $^3J_{6'a,6'b} = -13.14$ |
| | | $H_{6'b}$ | 3.5601 | |
| OMe$_2$ | 58.796 | OMe$_2$ | 3.500 | |
| OMe$_3$ | 60.386 | OMe$_3$ | 3.537 | |
| OMe$_4$ | 60.386 | OMe$_4$ | 3.506 | |
| OMe$_{3'}$ | 58.834 | OMe$_{3'}$ | 3.503 | |
| OMe$_{4'}$ | 58.493 | OMe$_{4'}$ | 3.467 | |

TABLE 6

500 MHz $^1$H NMR and 125 MHz $^{13}$C NMR Data (in N,N'-dimethylformamide-d$_7$) for 1',6,6'-Triamino-1',6,6'-trideoxy-2,3,3',4,4'-penta-O-methylsucrose

| $^{13}$C | | $^1$H | | |
|---|---|---|---|---|
| $C_1$ | 91.496 | $H_1$ | 5.5451 | $^3J_{1,2} = 3.45$ |
| $C_2$ | 83.009 | $H_2$ | 3.0817 | $^3J_{2,3} = 9.72$ |
| $C_3$ | 84.639 | $H_3$ | 3.3643 | $^3J_{3,4} = 8.96$ |
| $C_4$ | 81.890 | $H_4$ | 3.0755 | $^3J_{4,5} = 9.971$ |
| $C_5$ | 72.463 | $H_5$ | 3.7071 | $^3J_{5,6a} = 2.91$ |
| | | | | $^3J_{5,6b} = 5.57$ |
| $C_6$ | 43.105 | $H_{6a}$ | 2.8859 | $^2J_{6a,6b} = -13.45$ |
| | | $H_{6b}$ | 2.6679 | |
| $C_{1'}$ | 47.249 | $H_{1'a}$ | 3.8013 | $^2J_{1'a,1'b} = -12.17$ |
| | | $H_{1'b}$ | 3.7923 | |
| $C_{2'}$ | 105.700 | | | |
| $C_{3'}$ | 86.744 | $H_{3'}$ | 4.1201 | $^3J_{3',4'} = 7.17$ |
| $C_{4'}$ | 85.696 | $H_{4'}$ | 3.8808 | $^3J_{4',5'} = 7.21$ |
| $C_{5'}$ | 83.351 | $H_{5'}$ | 3.7695 | $^3J_{5',6'a} = 6.02$ |
| | | | | $^3J_{5',6'b} = 4.3$ |
| $C_{6'}$ | 45.593 | $H_{6'a}$ | 2.8534 | $^3J_{6'a,6'b} = -13.60$ |
| | | $H_{6'b}$ | 2.8280 | |
| OMe$_2$ | 59.761 | OMe$_2$ | 3.476 | |
| OMe$_3$ | 61.161 | OMe$_3$ | 3.516 | |
| OMe$_4$ | 61.046 | OMe$_4$ | 3.507 | |
| OMe$_{3'}$ | 59.460 | OMe$_{3'}$ | 3.507 | |

TABLE 6-continued

500 MHz $^1$H NMR and 125 MHz $^{13}$C NMR Data (in N,N'-dimethylformamide-d$_7$) for 1',6,6'-Triamino-1',6,6'-trideoxy-2,3,3',4,4'-penta-O-methylsucrose

| $^{13}$C | | $^1$H | |
|---|---|---|---|
| OMe$_{4'}$ | 59.000 | OMe$_{4'}$ | 3.449 |

TABLE 7

125 MHz $^{13}$C NMR Data (in N,N'-Dimethylformamide-d$_7$) for N,N',N'',-Tris[cis-amminedichloroplatinato]-1',6,6'-triamino-1',6,6'-trideoxy-2,3,3',4,4'-penta-O-methylsucrose (These structural assignments are tentative)

| | | | |
|---|---|---|---|
| $C_1$ | 89.22 | $C_{4'}$ | 83.48 |
| $C_2$ | 81.29 | $C_{5'}$ | 83.48 |
| $C_3$ | 78.25 | $C_{6'}$ | 48.64 |
| $C_4$ | 82.41 | OMe$_2$ | 58.56 |
| $C_5$ | 70.66 | OMe$_3$ | 60.40 |
| $C_6$ | 49.88 | OMe$_4$ | 60.51 |
| $C_{1'}$ | 54.57 | OMe$_{3'}$ | 58.78 |
| $C_{2'}$ | 103.63 | OMe$_{4'}$ | 59.41 |
| $C_{3'}$ | 87.87 | | |

TABLE 8

Cytotoxicity test of Diaminosucrose Platinum (II) compounds on human KB cell cultures

| | Drug Concentration ug/ml of culture medium | Incubation days | Cytotoxicity |
|---|---|---|---|
| Exp. 1 | | | |
| Sample No. 1 (Cisplatin) | 75 | 2 | 4+ |
| No. 2 | 125 | 2 | 4+ |
| No. 3 | 500 | 6 | 0 |
| No. 4 | 400 | 6 | 0 |
| No. 5 | 300 | 6 | 0 |
| Exp. 2 | | | |
| Sample No. 1 | 4 | 2 | 4+ |
| | 1 | 3 | 4+ |
| | 0.5 | 5 | 3+ |
| | 0.1 | 5 | 0 |
| Sample No. 2 | 125 | 3 | 4+ |
| | 50 | 5 | 0 |
| Exp. 3 | | | |
| Sample No. 6 | 500 | 2 | 4+ |
| | 100 | 3 | 0 |
| | 100 | 5 | 3+ |
| | 100 | 7 | 4+ |
| | 50 | 4 | 0 |
| | 50 | 5 | 2+ |
| | 50 | 7 | 3+ |
| | 50 | 9 | 4+ |
| | 10 | 6 | 0 |
| | 10 | 9 | 2+ |
| | 10 | 14 | 3+ |
| Exp. 4 | | | |
| Sample No. 7 | 250 | 1 | 2+ |
| | 250 | 4 | 4+ |
| | 100 | 4 | 4+ |
| | 50 | 4 | 3+ |
| | 50 | 6 | 4+ |
| | 20 | 4 | 2+ |
| | 20 | 6 | 3+ |
| | 20 | 8 | 4+ |
| | 10 | 6 | 2+ |
| | 10 | 8 | 3+ |
| | 10 | 10 | 3+ |

TABLE 9

Cytotoxicity test of Platinum compounds on human KB cell cultures

| | Drug Concentration ug/ml of culture medium | Incubation days | Cytotoxicity |
|---|---|---|---|
| Exp. 5 | | | |
| Sample No. 8 | 40 | 1 | 4+ |
| | 4 | 3 | 4+ |
| | 2 | 3 | 4+ |
| | 0.4 | 6 | 2+ |
| | 0.4 | 8 | 3+ |
| | 0.2 | 8 | 2+ |
| | 0.1 | 8 | 0 |
| Exp. 6 | | | |
| Sample No. 9 | 40 | 3 | 4+ |
| | 10 | 3 | 3+ |
| | 5 | 3 | 2+ |
| | 5 | 6 | 3+ |
| | 2 | 8 | 0 |
| Exp. 7 | | | |
| Sample No. 10 | 40 | 3 | 4+ |
| | 20 | 6 | 2+ |
| | 10 | 6 | 1+ |
| | 5 | 6 | 0 |
| Exp. 8 | | | |
| Sample No. 11 | 400 | 4 | 2+ |
| | 400 | 7 | 4+ |
| | 200 | 4 | 2+ |
| | 200 | 7 | 3+ |
| | 100 | 7 | 2+ |
| | 40 | 7 | 0+ |

TABLE 10

Effect of Diaminosucrose Platinum (II) compounds on intraperitoneally implanted Lewis lung carcinoma in mice

| Agent | Dose/mouse and schedule i.p. | Changes of body weight day to 7 | Mean survival days | No of mice survival/total | Increase in life span |
|---|---|---|---|---|---|
| Exp. 1 Control | | +2.8 g | 14.0 | 0/5 | |
| Sample No. 2 | 2 mg, day 1, 3 | +2.0 | 13.8 | 0/5 | −1% |
| Sample No. 6 | 2 mg, day 1, 3 | −3.0 | >43.4 | 3/5 | >210% |
| Exp. 2 Control | | +2.8 g | 11.2 | 0/6 | |
| Sample No. 7 | 0.5 mg day 1, 2, 3, 6 | −0.8 | >39.8 | 3/5 | >255% |

TABLE 11

Cytotoxicity Test of Sucrose Mono(platinum), Bis(platinum) & Tris(platinum) Complexes on Human KB Cell Cultures

| Agent | Drug concentration in culture medium | Incubation days | Cytotoxicity |
|---|---|---|---|
| cis-Platin | 0.5 μg/ml, ≈ 20 nM | 2 | 4+ |
| Mono(platinum) | >250 μg/ml | 3 | 4+ |
| Bis(platinum) | 10 μg/ml, 11.2 nM | 14 | 3+ |
| Tris(platinum) | 10 μg/ml, 7.9 nM | 10 | 3+ |

TABLE 12

Effect of Sucrose Mono(platinum), Bis(platinum), & Tris(platinum) Complexes on Intraperitoneally Implanted Lewis Lung Carcinoma in Mice

| Agent | Dose/mouse & schedule i.p. | Changes of body weight 1 to 7 | Mean survival days | No. of mice survival/total | Increase in life span |
|---|---|---|---|---|---|
| Control | | +2.8 g | 14.0 | 0/5 | |
| Mono(platinum) | 2 mg, day 1, 3 | +2.0 g | 13.8 | 0/5 | −1% |
| Bis(platinum) | 2 mg, day 1, 3 | −3.0 g | >43.4 | 3/5 | >210% |
| Control | | +2.8 g | 11.2 | 0/6 | |
| Tris(platinum) | 0.5 mg, day 1, 2, 3, 6 | −0.8 g | >39.8 | 3/5 | >2.55% |

TABLE 13

Effect of Dose of Sucrose Bis(platinum) Complex on Intraperitoneally Implanted Lewis Lung Carcinoma in Mice

| Agent | Dose/mouse & schedule i.p. | Changes of body weight day 1 to 7 | Survival days of individual mouse | Mean survival time | Increase in life span |
|---|---|---|---|---|---|
| Control | | +3.2 g | 17, 20, 21, 25 | 20.8 | |
| Bis(platinum) | 0.1 mg, day 2, 4 | +2.0 g | 45, >50, >50, >50 | >48.8 | >135% |

TABLE 14

Effect of Dose of Sucrose Bis(platinum) Complex on P388 Leukemia in Syngeneic DBA/2 Mice

| Agent | Dose/mouse & schedule i.p. | Changes of body weight day 1 to 2 | Survival days of individual mouse | Mean survival time | Increase in life span |
|---|---|---|---|---|---|
| Control | | +0.3 g | 7, 7, 8, 8, 8 | 7.6 | |
| Bis(platinum) | 2 mg, day 1 | −1.5 g | 10, 10, 14, 16, >30 | >16.0 | >111% |
| Bis(platinum) | 0.1 mg, day 1 | −0.2 g | 8, 8, 9, 9, 10 | >8.8. | 16% |

TABLE 15

Effect of Sucrose Bis(platinum) Complex on P388 Leukemia in Syngeneic DBA/2 Mice

| Agent | Dose/mouse & schedule i.p. | Changes of body weight day 1 to 2 | Survival days of individual mouse | Mean survival time | Increase in life span |
|---|---|---|---|---|---|
| Control | | +0.2 g | 7, 8, 9, 10, 10 | 8.8 | |
| Bis(platinum) | 1.0 mg, day 1 | −1.0 g | 10, 13, 14, 16, >30 | >16.6 | >89% |

What is claimed:

1. N,N'-bis[cis-amminedichloroplatinato]-6,6'-diamino-6,6'-dideoxy-1',2-anhydrosucrose.

2. N,N',N''-tris [cis-amminedichloroplatinato]-1',6,6'-triamino-1',6,6'-trideoxy-2,3,3',4,4'-penta-O-methylsucrose.

* * * * *